US011238959B2

(12) United States Patent
Horimoto et al.

(10) Patent No.: US 11,238,959 B2
(45) Date of Patent: Feb. 1, 2022

(54) BIOMARKER SEARCH METHOD, BIOMARKER SEARCH DEVICE, AND PROGRAM

(71) Applicant: NATIONAL INSTITUTE OF ADVANCED INDUSTRIAL SCIENCE AND TECHNOLOGY, Tokyo (JP)

(72) Inventors: Katsuhisa Horimoto, Tokyo (JP); Kazuhiko Fukui, Tokyo (JP)

(73) Assignees: NATIONAL INSTITUTE OF ADVANCED INDUSTRIAL SCIENCE AND TECHNOLOGY, Tokyo (JP); SOCIUM INC., Tokyo (JP)

( * ) Notice: Subject to any disclaimer, the term of this patent is extended or adjusted under 35 U.S.C. 154(b) by 936 days.

(21) Appl. No.: 15/550,761

(22) PCT Filed: Feb. 9, 2016

(86) PCT No.: PCT/JP2016/053846
§ 371 (c)(1),
(2) Date: Aug. 11, 2017

(87) PCT Pub. No.: WO2016/129601
PCT Pub. Date: Aug. 18, 2016

(65) Prior Publication Data
US 2018/0018424 A1 Jan. 18, 2018

(30) Foreign Application Priority Data
Feb. 13, 2015 (JP) .............................. JP2015-026059

(51) Int. Cl.
| | |
|---|---|
| *G16H 10/40* | (2018.01) |
| *G16B 30/00* | (2019.01) |
| *G16B 25/00* | (2019.01) |
| *G16B 40/00* | (2019.01) |
| *G16B 50/00* | (2019.01) |
| *G16B 20/00* | (2019.01) |
| *G16B 20/20* | (2019.01) |
| *G16B 25/10* | (2019.01) |
| *G16H 10/60* | (2018.01) |
| *C12Q 1/6883* | (2018.01) |

(52) U.S. Cl.
CPC ........... *G16H 10/40* (2018.01); *C12Q 1/6883* (2013.01); *G16B 20/00* (2019.02); *G16B 20/20* (2019.02); *G16B 25/00* (2019.02); *G16B 25/10* (2019.02); *G16B 30/00* (2019.02); *G16B 40/00* (2019.02); *G16B 50/00* (2019.02); *G16H 10/60* (2018.01); *C12Q 2600/154* (2013.01); *C12Q 2600/158* (2013.01)

(58) Field of Classification Search
CPC ........ G16B 30/00; G16B 40/00; G16B 20/00; G16B 25/00; G16B 50/00; G16B 25/10; G16H 10/60; G16H 10/40; C12Q 1/6883
USPC .......................................................... 702/19
See application file for complete search history.

(56) References Cited

U.S. PATENT DOCUMENTS

| | | |
|---|---|---|
| 2007/0213939 A1 | 9/2007 | Liew et al. |
| 2009/0208942 A1 | 8/2009 | Liew et al. |
| 2012/0109615 A1 | 5/2012 | Yun et al. |
| 2013/0013214 A1 | 1/2013 | Liew et al. |
| 2013/0259847 A1 | 10/2013 | Vishnudas et al. |
| 2015/0019190 A1 | 1/2015 | Danter |
| 2015/0191796 A1 | 7/2015 | Liew et al. |
| 2015/0278433 A1 | 10/2015 | Aihara et al. |

FOREIGN PATENT DOCUMENTS

| | | |
|---|---|---|
| JP | 2012-94143 A | 5/2012 |
| JP | 2013-150612 A | 8/2013 |
| JP | 2015-509224 A | 3/2015 |
| WO | 2014/050160 A1 | 4/2014 |

OTHER PUBLICATIONS

International Search Report for PCT/JP2016/053846, dated Mar. 15, 2016, and its English translation provided by WIPO.
Written Opinion of the International Search Authority for PCT/JP2016/053846, dated Mar. 15, 2016, and its English translation provided by WIPO.
International Preliminary Report on Patentability Chapter I dated Aug. 15, 2017, and its English translation provided by WIPO.
"Challenges for Japan Towards Efficiency Improvement of Drug Discovery Process from Viewpoint of Patent Application Trends in Biomarker-Related Research Field", Yuji Toriyama, Research Paper Series No. 46, The Office of Pharmaceutical Industry Research Institute, Oct. 2009 (Partial English translation provided by applicant).

*Primary Examiner* — Jerry Lin
(74) *Attorney, Agent, or Firm* — Ladas & Parry, LLP (57) ABSTRACT

A device for searching a biomarker to be used for determining whether or not a first treatment has an effect on a disease, the biomarker search device includes: a first storage; a second storage storing; a third storage; a fourth storage; a signature molecular information detector; a regression analyzer; a network generator; and a biomarker determinator.

13 Claims, 8 Drawing Sheets

[BEFORE TREATMENT]

| PATIENT ID | LVDd | LVEF | LAD | ... |
|---|---|---|---|---|
| p00001 | 109 | 5 | 44 | ... |
| p00002 | 77 | 26 | 54 | ... |
| p00003 | 46 | 20 | 44 | ... |
| p00004 | 61.7 | 13 | 46.5 | ... |
| ⋮ | ⋮ | ⋮ | ⋮ | ⋮ |
| p09000 | 71 | 31 | 70 | ... |

FIG.3

[AFTER TREATMENT]

| PATIENT ID | LVDd | LVEF | LAD | ... |
|---|---|---|---|---|
| p00001 | 106 | 5 | 44 | ... |
| p00002 | 69 | 15 | 28 | ... |
| p00003 | 46 | 20 | 44 | ... |
| p00004 | 80.4 | 25 | 37 | ... |
| ⋮ | ⋮ | ⋮ | ⋮ | ⋮ |
| p09000 | 71 | 31 | 70 | ... |

BIOMARKER SEARCH METHOD, BIOMARKER SEARCH DEVICE, AND PROGRAM

CROSS REFERENCE TO RELATED APPLICATIONS

The present application is the U.S. national phase of PCT Application No. PCT/JP2016/053846 filed on Feb. 9, 2016, which claims priority to Japanese Patent Application No. 2015-026059 filed on Feb. 13, 2015, the disclosures of which are incorporated herein by reference in their entireties.

TECHNICAL FIELD

The present invention relates to a method and device for searching a biomarker used in the fields of individualized medical care and drug discovery.

BACKGROUND ART

Conventionally, biomarkers that sensitively reflect the onset of disease due to specific gene expression, drug responsiveness due to genetic variation (genetic polymorphism) or the like have been known in the fields of individualized medical care and drug discovery.

Disease status varies depending on individual patients, and the same medicine works for some patients, and does not work for other patients. In the past, a method of actually administering a medicine and observing the effect was adopted. In individualized medical care, in addition to general medical information, it is possible to appropriately treat individual patients, by grasping genetic background, physiological state and disease status of the patient, by biomarkers.

Also, in the field of drug discovery, the number of newly approved medicines decreases year by year, but the biggest cause is the low probability of success in clinical trials. In clinical trials, new drugs are administered to a randomized patient group, and the effects and side effects thereof are tested. However, genetic background, physiological state and disease status and the like are different depending on individual patients, as described above, thus there were cases in which no effect was observed, or some side effects occurred in some patients. When patients having effects of new drugs and patients having side effects of new drugs can be stratified using biomarkers, the probability of success in clinical trials can be increased.

CITATION LIST

Non-Patent Literature

Non-Patent Literature 1: "Challenges for Japan Towards Efficiency Improvement of Drug Discovery Process from Viewpoint of Patent Application Trends in Biomarker-Related Research Field" edited by Yuji Toriyama, Research Paper Series No. 46, The Office of Pharmaceutical Industry Research Institute (October 2009)

SUMMARY OF INVENTION

Technical Problem

As described above, although biomarkers are important in the fields of individualized medical care, drug discovery and the like, the development of biomarkers is not easy.

Therefore, in view of such background, the present invention provides a biomarker search method and device capable of searching a biomarker.

Solution to Problem

A method, according to the present invention, for searching a biomarker to be used for determining whether or not a predetermined treatment has an effect on a disease, includes: a step of reading, from a storage means, omics information of a plurality of patients before treatment and omics information of control, and detecting signature molecular information peculiar to disease from the omics information comprising a plurality of molecular information items, based on the read omics information of patients and the read omics information of control; and a step of obtaining a biomarker from the signature molecular information, wherein in the step of obtaining the biomarker, a process of selecting at least one molecular information item to be processed from the signature molecular information, a process of reading the clinical information of a plurality of patients before treatment and the information of the effect of treatment in a plurality of patients from the storage means, and carrying out a regression analysis, using the effect of treatment as an objective variable, and using the clinical information before treatment, and variable data of the molecular information to be processed as explanatory variables, a process of generating a network structure based on partial correlation between each of nodes, using the effect of treatment, the clinical information before treatment, and the molecular information to be processed as the nodes, when the determination coefficient of the regression analysis is equal to or more than a predetermined threshold value, and a process of determining whether or not there is a causal relationship equal to or more than a predetermined threshold value between the molecular information to be processed and the effect of treatment in the network structure, and determining the molecular information to be processed as a biomarker, when there is a causal relationship equal to or more than a predetermined threshold value are repeated.

Treatment includes various treatments such as treatment by administration of medicine, treatment with ventricular assist system (VAS), treatment with surgery and laser, and treatment with a stent or the like, and the like. Also, the effect of treatment is the degree that patients were recovered or are to be recovered by treatment, and includes drug efficacy by administration of medicine.

Omics information is comprehensive molecular information such as methylation of genes, expression of mRNA, expression of protein, protein conformation, single nucleotide polymorphism (SNP), and all metabolites in cells, and the information amount thereof is huge. According to the present invention, the signature molecular information of a disease is first obtained, and a biomarker is searched from them, thus the biomarker can be efficiently searched. In addition, variation of omics information is large, and noise often occurs, unlike genomic data. However, in the network structure, the influence of noise is avoided by drawing a causal inference between the effect of treatment and the molecular information, and an appropriate biomarker can be obtained.

The biomarker search method according to the present invention may includes a step of reading clinical information of a plurality of patients before and after treatment from a storage module, and obtaining the effect of treatment based on the clinical information before and after treatment.

With this configuration, it becomes possible to search a biomarker even when the effect of treatment is not stored in advance, and the effect of treatment can be quantitatively analyzed. In order to obtain the effect of treatment, it is not necessary to use all clinical information, and it is also acceptable to use only clinical information predetermined by a doctor or the like.

In the biomarker search method according to the present invention, methylation level information of genes, expression information of mRNA, and expression information of proteins may be used as the omics information.

With this configuration, biomarkers can be properly searched, based on multilateral omics information.

In the biomarker search method according to the present invention, the step of obtaining a biomarker may determine a predetermined number of molecular information items as a biomarker from one having a strong causal relationship with the effect of treatment.

Thus, a user can select a biomarker to be used for medical care, drug discovery or the like, from a predetermined number of omics information items.

A device, according to the present invention, for searching a biomarker to be used for determining whether or not a predetermined treatment has an effect on a disease, the biomarker search device includes: a means for storing clinical information of a plurality of patients before treatment; a means for storing omics information of a plurality of patients before treatment; a means for storing omics information of control; a means for storing information indicating the effect of treatment in a plurality of patients; a means for detecting signature molecular information peculiar to disease from the omics information comprising a plurality of molecular information items, based on the omics information of patients and the omics information of control; a regression analyzer for carrying out a regression analysis, using the effect of treatment as an objective variable, and using the clinical information before treatment, and variable data of at least one molecular information item selected as molecular information to be processed from the signature molecular information as explanatory variables; a network generator for generating a network structure based on partial correlation between each of nodes, using the effect of treatment, the clinical information before treatment, and the selected molecular information to be processed as the nodes, when the determination coefficient of the regression analysis by the regression analyzer is equal to or more than a predetermined threshold value; and a biomarker determinator for determining whether or not there is a causal relationship equal to or more than a predetermined threshold value between the molecular information to be processed and the effect of treatment in the network structure, and determining the molecular information to be processed as a biomarker, when there is a causal relationship equal to or more than a predetermined threshold value.

The biomarker search device according to the present invention may further includes: a means for storing clinical information of a plurality of patients after treatment, and a means for obtaining the effect of treatment based on the clinical information before and after treatment, wherein the biomarker search device stores information of the obtained effect of treatment.

In the biomarker search device according to the present invention, wherein methylation level information of genes, expression information of mRNA, and expression information of proteins are used as the omics information.

A program according to the present invention is a program for making a computer to execute the above method according to the present invention.

Advantageous Effects of Invention

According to the present invention, efficient search can be performed by searching a biomarker from signature molecular information, after obtaining the signature molecular information peculiar to disease from omics information. In addition, the present invention has an effect capable of avoiding the influence of noise to obtain an appropriate biomarker, by drawing a causal inference on the network structure.

BRIEF DESCRIPTION OF DRAWINGS

FIG. 6(*a*) is a diagram showing an example of a network structure. FIG. 6(*b*) is a diagram showing another example of a network structure.

DESCRIPTION OF EMBODIMENTS

Hereinafter, a biomarker search device and biomarker search method according to an embodiment of the present invention will be described with reference to the drawings. In the present embodiment, an example of dilated cardiomyopathy is given. As a treatment for dilated cardiomyopathy, there is a method of applying a ventricular assist system (VAS), but its recovery rate is extremely different depending on patients. If the recovery rate by applying a VAS can be predicted, it becomes easier to judge whether or not the VAS should be put. In the present embodiment, an example of searching a biomarker for predicting the recovery rate (effect of treatment) when the VAS is applied is given. The present invention is not limited to the examples described in the following embodiments, and can be applied for searching a biomarker for other various treatments.

Figure 1:
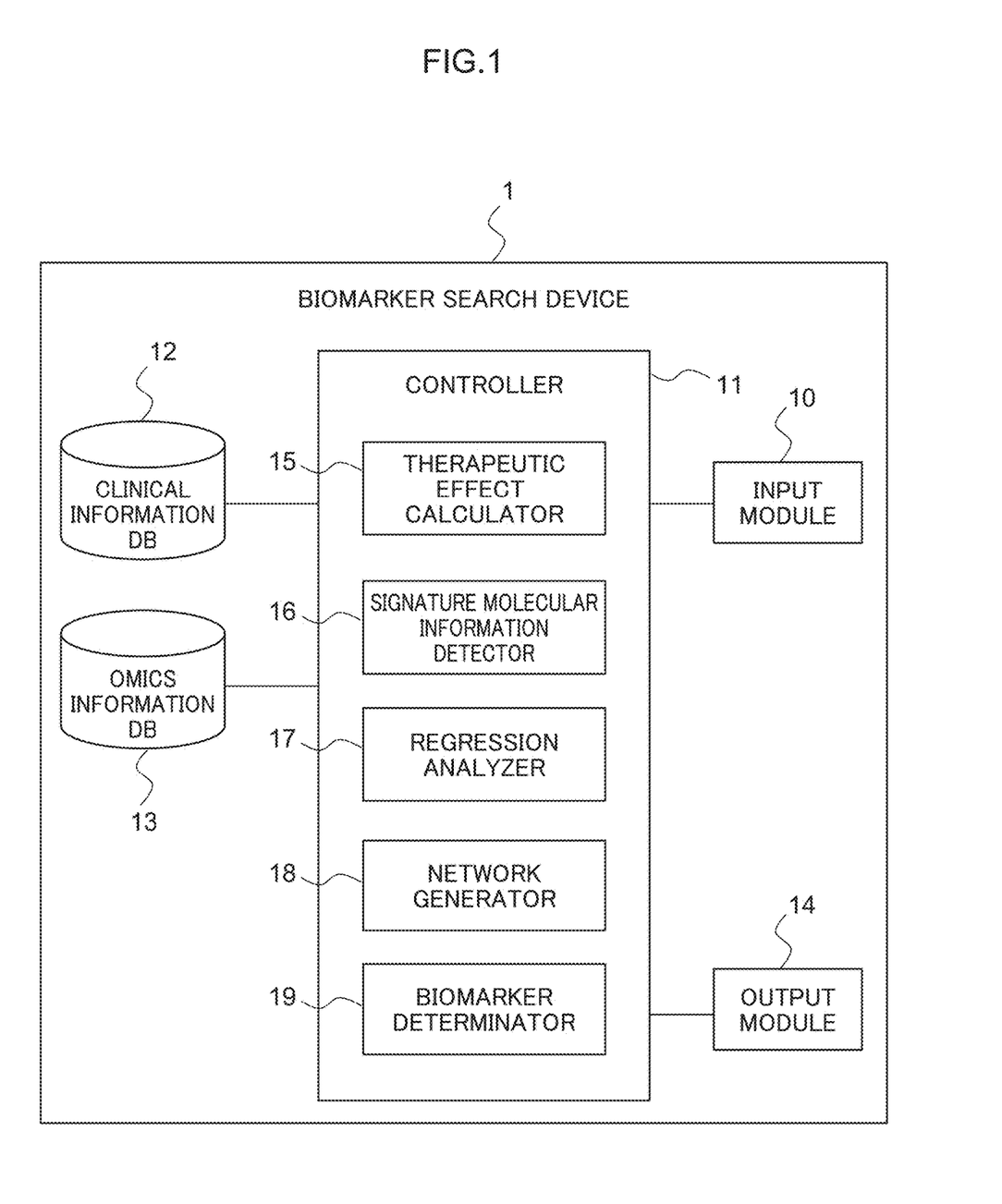
FIG. 1 is a diagram showing a configuration of a biomarker search device according to an embodiment.

FIG. 1 is a diagram showing a configuration of a biomarker search device 1 according to an embodiment. The biomarker search device 1 includes an input module 10 for inputting information, a controller 11 for performing processing for searching a biomarker, a clinical information database (hereinafter referred to as "clinical information DB".) 12 which stores clinical information of patients, an omics information database (hereinafter referred to as "omics information DB".) 13 which stores omics information of patients and control, and an output module 14 for outputting data of the searched biomarker.

The biomarker search device 1 is constituted by a computer having a CPU, a RAM, a ROM, a display, a keyboard, a mouse, a communication interface, and the like. A program for searching a biomarker is stored in the ROM, and the CPU reads the program from the ROM and executes it, whereby the computer searches the biomarker.

Figure 2:
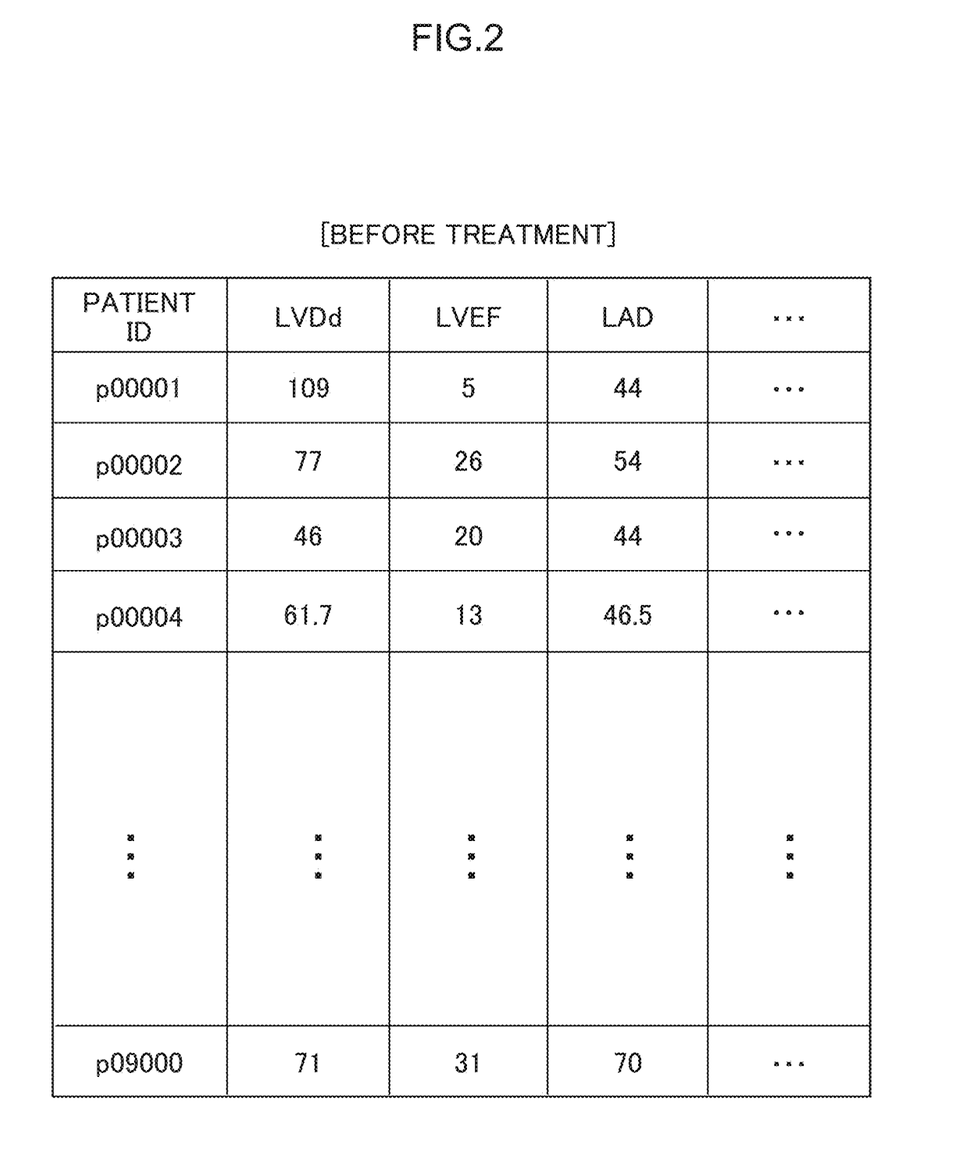
FIG. 2 is a diagram showing an example of data stored in a clinical information database.
Figure 3:
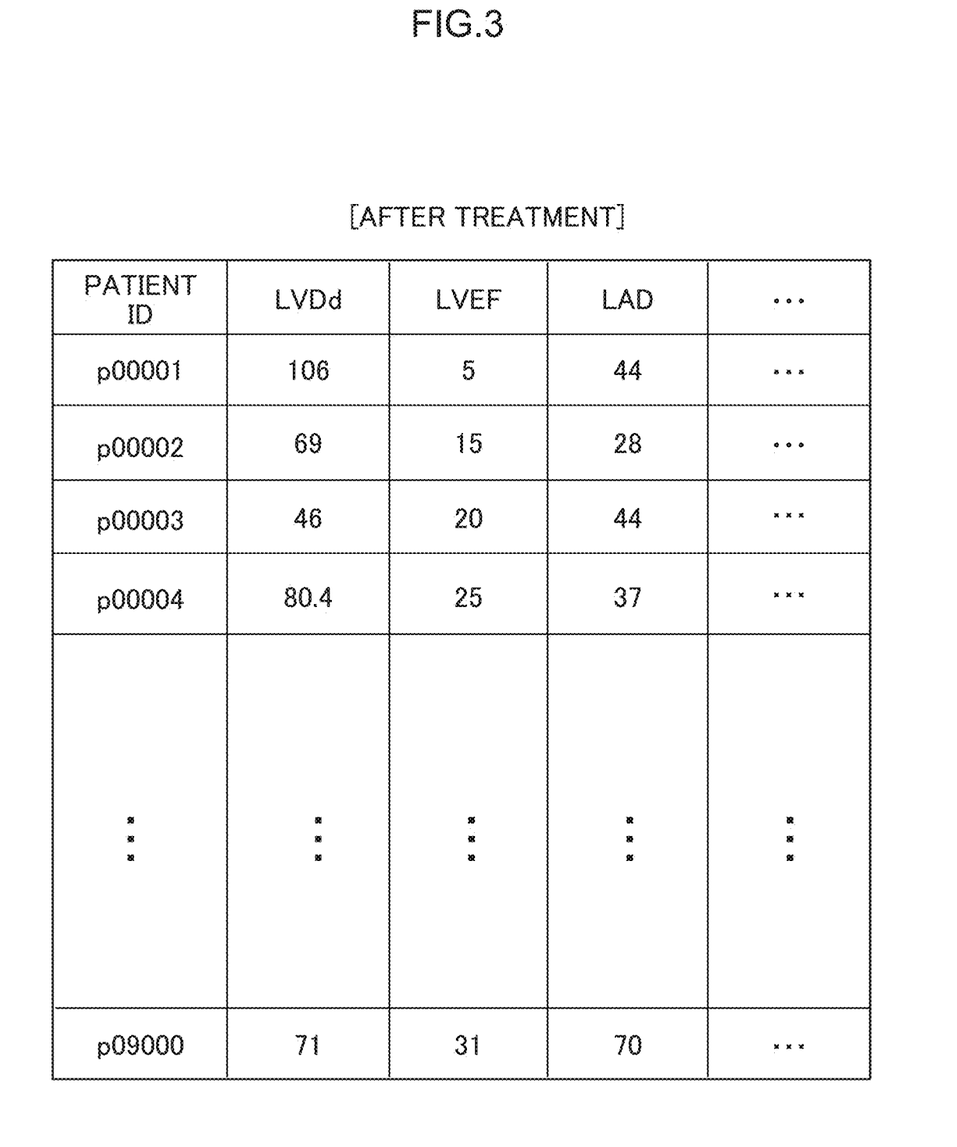
FIG. 3 is a diagram showing an example of data stored in a clinical information database.

FIG. 2 is a diagram showing an example of clinical information of patients before treatment stored in the clinical information DB 12, and FIG. 3 is a diagram showing an example of clinical information of patients after treatment similarly stored in the clinical information DB 12. As shown in FIGS. 2 and 3, as the clinical information, values indicating the degrees of dilated cardiomyopathy such as Left Ventricular Dimension at Diastole (LVDd), left ventricular ejection fraction (LVEF), and Left anterior descending coronary artery (LAD) are stored.

Figure 4:
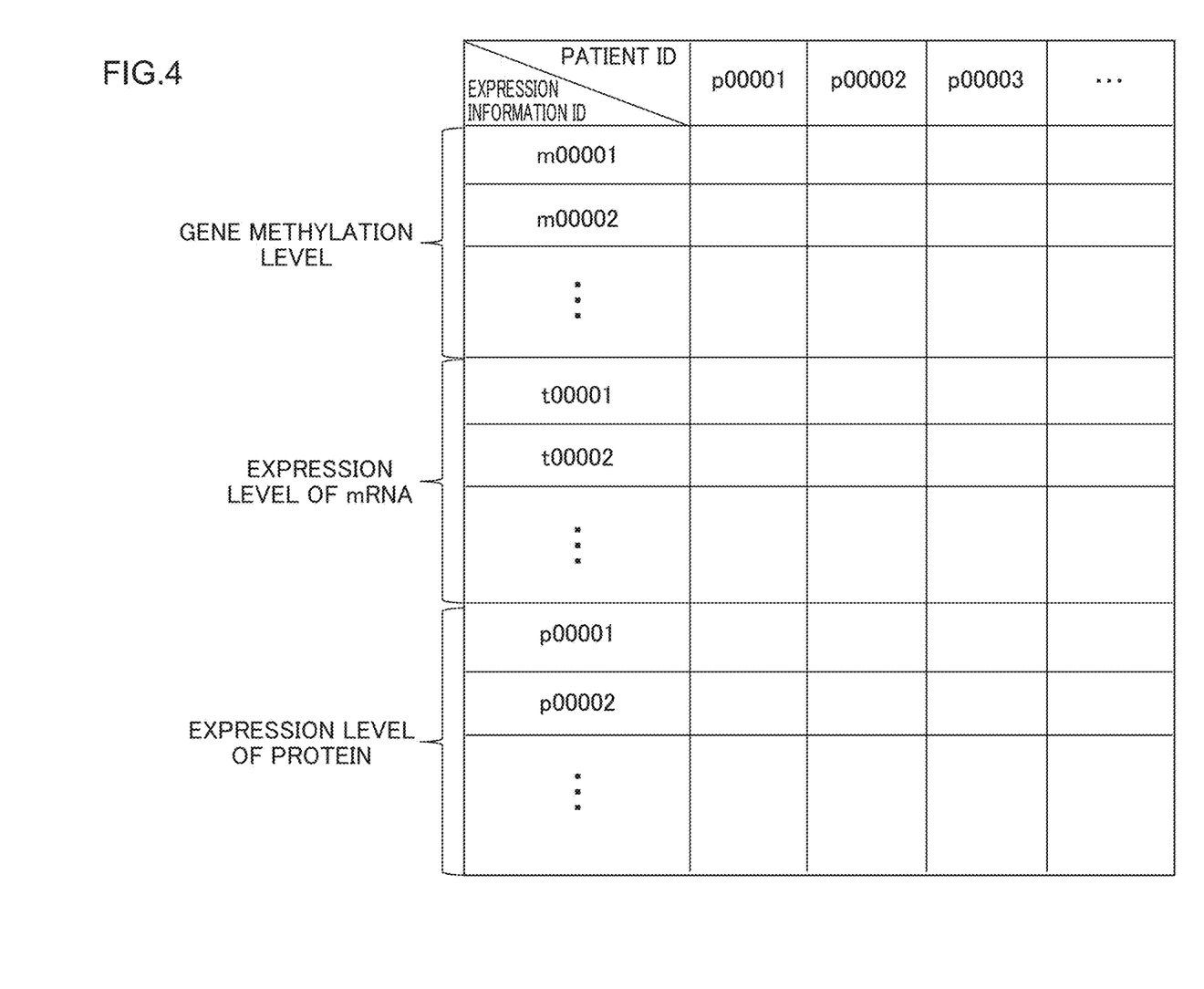
FIG. 4 is a diagram showing an example of data stored in an omics information database.

FIG. 4 is a diagram showing an example of data stored in the omics information DB 13. In each of the patients, three layers of molecular information of gene methylation level, expression level of mRNA and expression level of protein are stored in the omics information DB 13. Omics information is a gathering of such comprehensive molecular information. In the present embodiment, by using three layers of expression information, a possibility that a biomarker having high correlation with the effect of treatment can be found is increased. Although not shown in FIG. 4, the omics information DB 13 stores omics information of control (healthy person) not having a predetermined disease, in addition to the omics information of patients.

Returning to FIG. 1, the configuration of the controller 11 will be described. The controller 11 has a therapeutic effect calculator 15, a signature molecular information detector 16, a regression analyzer 17, a network generator 18, and a biomarker determinator 19.

The therapeutic effect calculator 15 has a function of quantitatively calculating the effect of treatment, using clinical information of patients before and after the treatment. The therapeutic effect calculator 15 may calculate the effect of treatment according to the degree of improvement in predetermined clinical information or may calculate the effect of treatment according to the degree of improvement in a plurality of clinical information items. In the present embodiment as an example of dilated cardiomyopathy, the degree of treatment is calculated according to the degree of improvement in LVDd. That is, the therapeutic effect calculator 15 reads the data of LVDd before and after the treatment from the clinical information DB 12, and calculates the effect of treatment by, Effect of treatment=LVDd (after treatment)−LVDd (before treatment).

The signature molecular information detector 16 reads the omics information of patients and the omics information of control from the omics information DB 13, and calculates signature molecular information with a large variation from control in a patient having a predetermined disease, based on the omics information of patients and the omics information of control. As described above, the three layers of molecular information of gene methylation level, expression level of mRNA and expression level of protein are stored in the omics information DB 13, and the information of genes in each layer is handled as separate information. For example, in a case where data on gene methylation information for gene A, expression level of mRNA for gene A, and protein expression level for gene A are stored, even when the expression level of mRNA for gene A is variable data peculiar to disease and detected as signature molecular information, the gene methylation level and expression level of protein of gene A are not automatically detected as signature molecular information.

In detection of signature molecular information, the method described in Japanese Patent Application No. 2014-173382 previously filed by the present applicant may be used. In this method, genes included in a known pathway are identified from the omics information, and clustering is performed using the omics information of the identified genes. When the patients and control can be clustered with a predetermined accuracy by the clustering, this pathway is regarded as a disease-specific pathway, and signature molecular information is obtained from the pathway. By using this method, pathway compatibility is determined by comparing only molecular information of a small number of genes included in the pathway, thus a disease-specific pathway can be extracted while suppressing the influence of noise, eventually, signature molecular information can be extracted.

Figure 5:
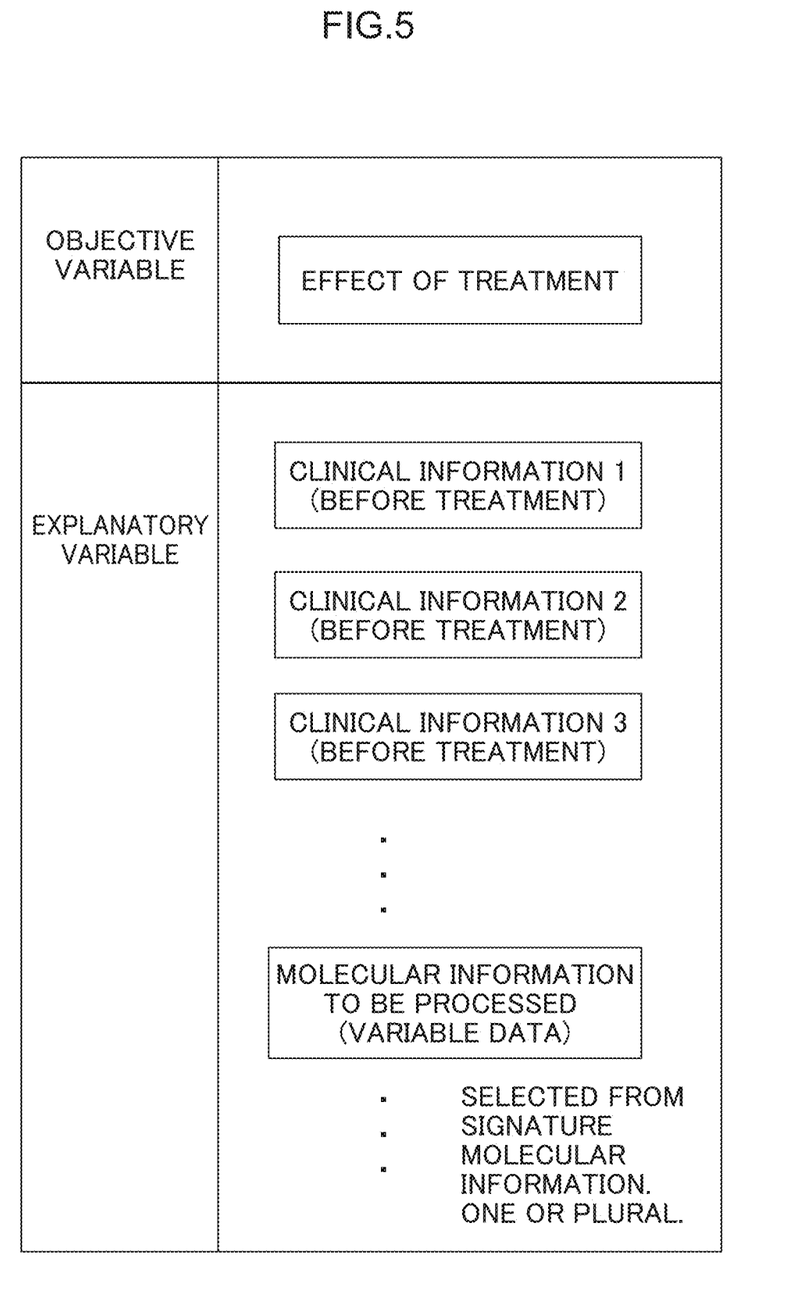
FIG. 5 is a diagram for describing variables used in regression analysis.

FIG. 5 is a schematic diagram for describing variables used in the regression analyzer 17. The regression analyzer 17 uses the effect of treatment calculated by the therapeutic effect calculator 15 as an objective variable. Those which the regression analyzer 17 uses as explanatory variables are a plurality of clinical information items before treatment and variable data of the molecular information to be processed. The variable data is data on how much the molecular information of patients varies as compared to the molecular information of control. The information before treatment is used as an explanatory variable because the biomarker sought in the present embodiment is for predicting the therapeutic effect by VAS application on the basis of the information before treatment.

As the molecular information, one molecular information item selected from the signature molecular information or a combination of a plurality of molecular information items is used. Since the molecular information selected here is molecular information to be subjected to verification processing as to whether or not there is a correlation with the effect of treatment as described later, it is referred to as "molecular information to be processed" in the present application.

The number of the molecular information items to be processed is desirably 1 or 2 to 3, but 4 to 5 molecular information items may be used. When using a lot of molecular information items, the accuracy of prediction increases by that much. However, a plurality of biomarkers has to be observed, thus the value as a biomarker is declined. How much molecular information is used as a biomarker may be, for example, inputted by the user from the input module 10.

When the determination coefficient is equal to or more than the predetermined threshold value, the regression analyzer 17 determines that the molecular information to be processed is recognized as having some influence on the effect of treatment, and proceeds to processing by the network generator 18. Here, as the determination coefficient, fitness is evaluated by adding a variable with a regression coefficient, and a degree of freedom adjusted determination coefficient or a modified determination coefficient obtained by modifying the degree of freedom is used. When the determination coefficient of the regression analysis is less than the predetermined threshold value, another molecular information item to be processed is selected from the signature molecular information, and a regression analysis is performed. In this way, by sequentially selecting another molecular information item to be processed and carrying out a regression analysis, molecular information related to the effect of treatment can be obtained from the signature molecular information.

Next, the network generator 18 will be described. The network generator 18 has a function of generating a network structure using the molecular information that passed a check by the regression analysis, a plurality of clinical information items and the effect of treatment as nodes. The network generator 18 obtains a partial correlation coefficient between each of nodes (molecular information, a plurality of clinical information items, effect of treatment), and generates a network structure based on the partial correlation coefficient. The network generator 18 determines that there is a correlation between the nodes having partial correlation coefficients equal to or more than the predetermined threshold value and connects the nodes, and determines that there is no correlation between the nodes having partial correlation coefficients less than the predetermined threshold value and does not connect the nodes.

Figure 6:
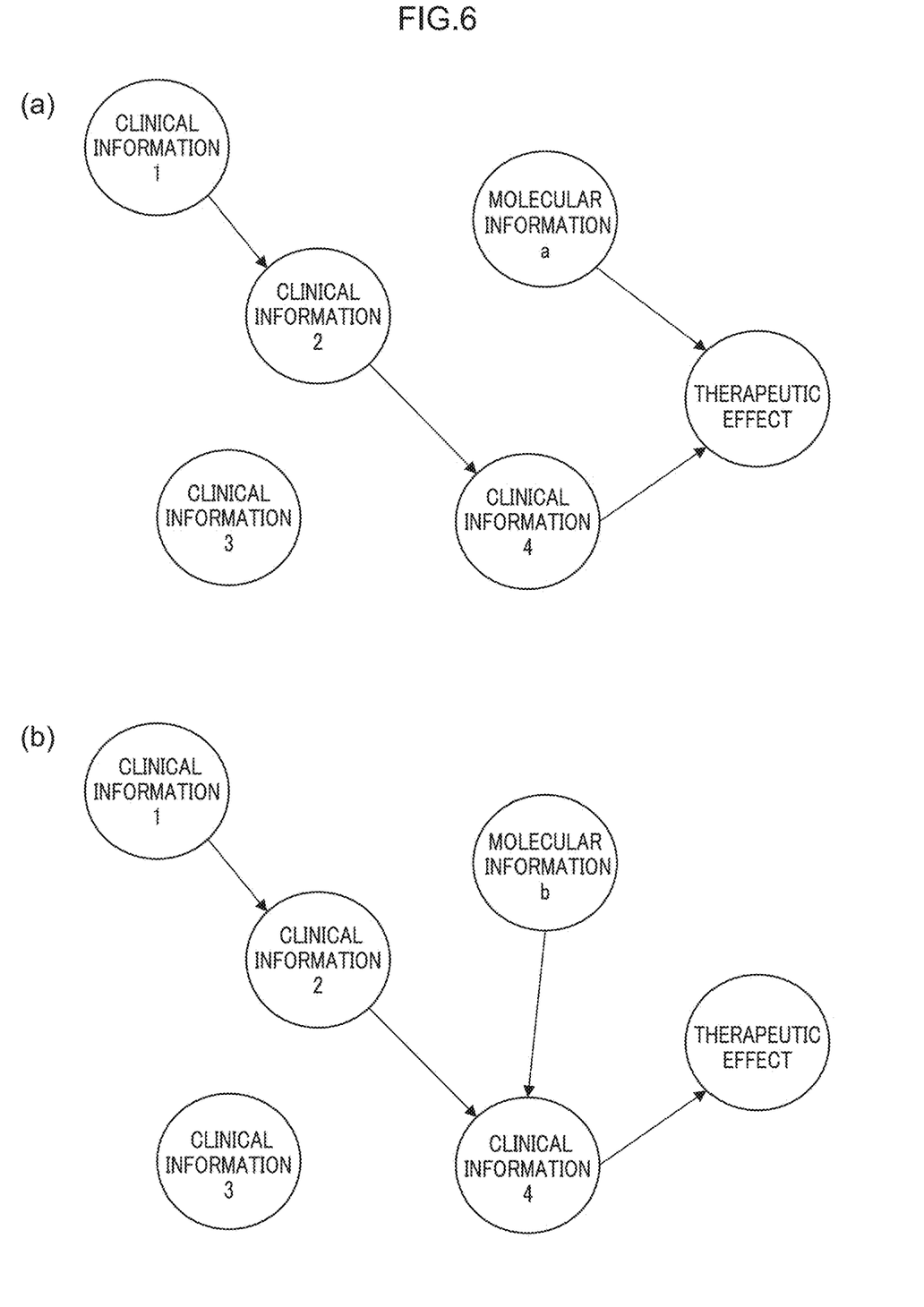

FIGS. 6(a) and 6(b) are diagrams showing an example of the network structure generated by the network generator 18. In FIGS. 6(a) and 6(b), using the molecular information, the clinical information and the therapeutic effect as nodes, the nodes with partial correlation coefficients equal to or more than a predetermined threshold value are connected to describe the network structure, based on the partial correlation coefficients between the each of nodes. Since the partial correlation coefficient is used for network generation, it is possible to obtain the correlation between two variables by eliminating the influence of other nodes.

In the example shown in FIG. 6(a), it can be seen that the node of molecular information "a" and the node of therapeutic effect are linked, and there is a direct correlation between them. In the example shown in FIG. 6(b), it can be seen that the node of omics information "b" is linked to the node of the therapeutic effect via clinical information 4, and there is an indirect correlation between the omics information "b" and therapeutic information. In FIGS. 6(a) and 6(b), no link is established in the node of clinical information 3, and it shows that the clinical information 3 has no predetermined correlation with other clinical information, the therapeutic effect, and the molecular information.

The biomarker determinator 19 determines a biomarker, based on the network structure generated by the network generator 18. The biomarker search device 1 of the present embodiment determines molecular information having a direct link with a therapeutic effect, that is, a causal relationship, as a biomarker. The biomarker search device 1 of the present embodiment determines the molecular information "a" shown in FIG. 6(a) as a biomarker. When a biomarker is to be used as molecular information indirectly connected by a link, that is, having an indirect causal relationship, with the therapeutic effect, the biomarker search device 1 determines the molecular information "b" shown in FIG. 6(b) as a biomarker, in addition to the molecular information "a" shown in FIG. 6(a). In the case of an indirect link, it may be determined whether or not to use it as a biomarker depending on the number of intervening nodes.

The output module 14 has a function of outputting data indicating the biomarker determined by the biomarker determinator 19.

Figure 7:
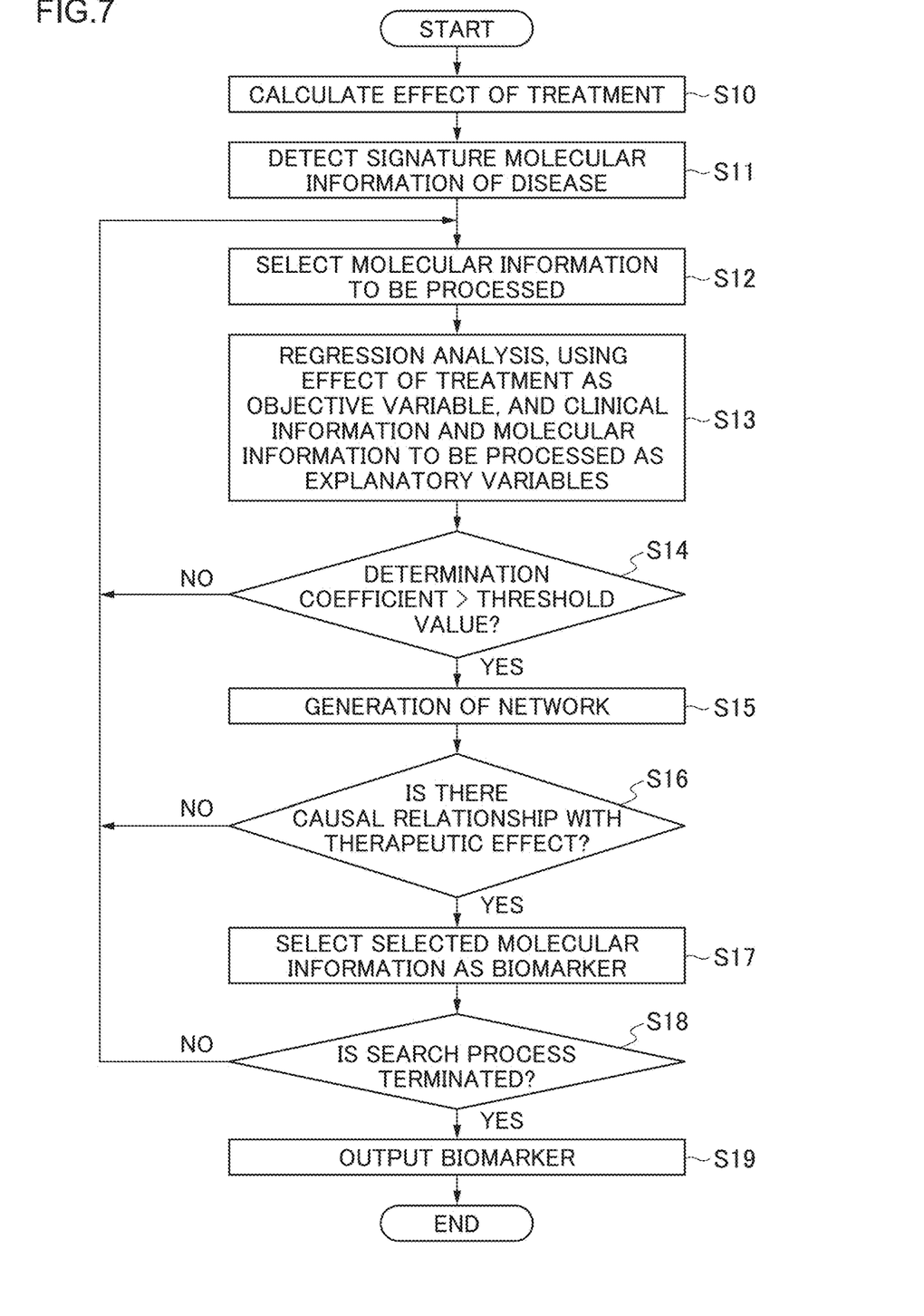
FIG. 7 is a diagram showing the operation of the biomarker search device according to an embodiment.
Figure 8:
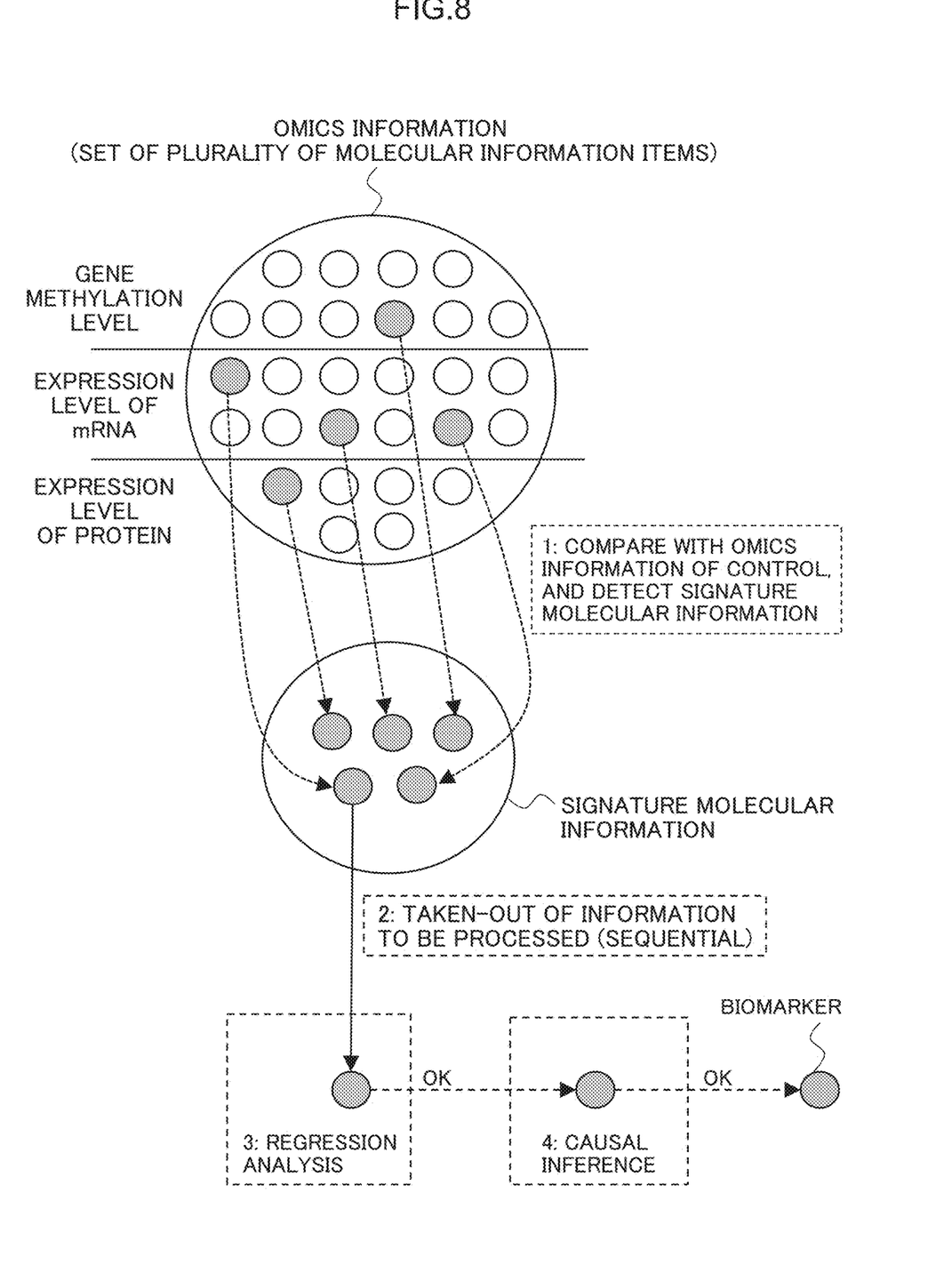
FIG. 8 is a diagram showing a state that molecular information is narrowed down by processing of the biomarker search device of an embodiment.

FIG. 7 is a flowchart showing the operation of the biomarker search device 1 of the present embodiment. FIG. 8 is a diagram showing how the molecular information is narrowed down by the processing of the biomarker search device 1 of the present embodiment. First, the biomarker search device 1 calculates the effect of treatment when a predetermined treatment is performed (S10). In the present embodiment, among a plurality of clinical information items, the degree of improvement in LVDd before and after the treatment is calculated as the effect of treatment.

Next, the biomarker search device 1 reads omics information of patients and omics information of control from the omics information DB 13, and detects signature molecular information peculiar to disease (S11), based on variable data of the omics information of patients and the omics information of control. As shown in FIG. 8, the omics information includes much molecular information relating to gene methylation level, expression level of mRNA, and expression level of protein. Shaded in FIG. 8 is signature molecular information which varies largely from the control, and in this step, it can be seen that the omics information is narrowed down to the signature molecular information.

Description will be made, returning to FIG. 7. The biomarker search device 1 selects one molecular information item to be processed from the signature molecular information (S12) and determines whether or not the molecular information becomes a biomarker. Specifically, the biomarker search device 1 firstly carries out a regression analysis on whether it is possible to explain the therapeutic effect which is an objective variable, using the molecular information to be processed together with a plurality of clinical information items as explanatory variables (S13). As a result of the regression analysis, it is determined whether or not the determination coefficient is larger than a predetermined threshold value (S14), and when the determination coefficient is larger than the predetermined threshold value (YES in S14), the process proceeds to the generation of the network structure (S15). When the determination coefficient is equal to or less than the predetermined threshold value (NO in S14), the molecular information to be processed is excluded from the biomarker candidates, and then molecular information to be confirmed as to whether it can be a biomarker is selected (S12). As shown in FIG. 8, the molecular information to be processed is taken out from a plurality of molecular information items extracted as signature molecular information, and a regression analysis is performed using the taken-out molecular information as an explanatory variable. As a result, when the determination coefficient is equal to or more than the predetermined threshold value, the process proceeds to causal inference using the network structure.

Description will be made again, returning to FIG. 7. The biomarker search device 1 generates a network structure, based on partial correlation between each of nodes, using molecular information in which the determination coefficient obtained by the regression analysis is larger than a predetermined threshold value, a plurality of clinical information items and the therapeutic effect as the nodes (S15). Then, in the generated network structure, the biomarker search device 1 determines whether or not there is a direct causal relationship between the molecular information and the therapeutic effect (S16). As a result, when it is determined that there is a direct causal relationship (YES in S16), the biomarker search device 1 determines the molecular information as a biomarker (S17). When it is determined that there is no causal relationship between the molecular information and the therapeutic effect (NO in S16), the molecular information to be processed is excluded from the biomarker candidates, and then molecular information to be confirmed as to whether it can be a biomarker is selected (S12). As shown in FIG. 8, as a result of the regression analysis, the causal inference using the network structure is drawn on the molecular information in which the determination coefficient is equal to or more than the predetermined threshold value, and when there is a causal relationship with the therapeutic effect, the molecular information is determined as a biomarker.

Subsequently, the biomarker search device 1 determines whether or not the search process is terminated (S18), and when it is determined to terminate the process (YES in S18), the biomarker search device 1 outputs the molecular information determined as a biomarker so far. When it is determined that the search process is not terminated (NO in S18), the selected molecular information is excluded from the biomarker candidates, and then molecular information to be confirmed as to whether it can be a biomarker is selected (S12). Here, the termination condition of the search process is when all the molecular information detected as signature molecular information is confirmed.

The configuration and operation of the biomarker search device 1 of the present embodiment have been described above. The biomarker search device 1 of the present embodiment employs a configuration in which signature molecular information peculiar to disease is obtained from omics information and a biomarker is searched from the signature molecular information. Thus, it is possible to efficiently search a biomarker from the huge amount of the omics information.

In addition, the biomarker search device 1 of the present embodiment employs a configuration in which whether there is a causal relationship between the effect of treatment and the molecular information to be processed in the network structure generated using partial correlation coefficient is determined, and the molecular information is selected as a biomarker when there is a causal relationship. Variation of omics information is large, and noise often occurs, unlike genomic data, but the influence of noise can be suppressed by drawing a causal inference.

The biomarker discovered in the biomarker search device 1 of the present embodiment predicts the effect and side effect of a medicine before dosing, and can be used as a "patient stratification marker" that stratifies patients for which the medicine effectively works and patients for which the medicine does not effectively work. Also, the clinical test that causes this stratification is called "companion diagnosis", and can be also useful for the development of "companion diagnostic agent" for measuring the biomarker found in the biomarker search device 1 of the present embodiment.

Further, the biomarker search device 1 of the present embodiment first carries out a regression analysis to generate a network structure when a determination coefficient equal to or more than a predetermined threshold value is obtained in the regression analysis. The efficiency of the calculation process is increased by making the generation of the network structure with larger calculation load than the regression analysis as a later process.

The biomarker search device and biomarker search method of the present invention have been described in detail with reference to the embodiments above, but the present invention is not limited to the above-described embodiments.

In the embodiments described above, the example in which the biomarker search device 1 includes the therapeutic effect calculator 15 and calculates the therapeutic effect based on the clinical information before and after the treatment has been described, but the therapeutic effect may be previously inputted by the doctor's judgment and stored. Thus, the therapeutic effect calculator 15 can be omitted.

When a plurality of molecular information items satisfying a predetermined threshold value is found in the regression analysis and the causal inference using the network structure, the biomarker determinator 19 may determine a predetermined number of molecular information items having a large causal relationship with the therapeutic effect as a biomarker. By presenting a plurality of biomarkers, the user can select an easily manageable biomarker from them. Also, when outputting a biomarker, it may be outputted together with the strength of the causal relationship with the therapeutic effect. Thus, the user presented with the searched biomarker can easily determine which biomarker should be used.

INDUSTRIAL APPLICABILITY

The present invention has an effect capable of avoiding the influence of noise to obtain an appropriate biomarker, and is useful for the development of biomarkers.

REFERENCE SIGNS LIST

1 Biomarker search device
10 Input module
11 Controller
12 Clinical information DB
13 Omics information DB
14 Output module
15 Therapeutic effect calculator
16 Signature molecular information calculator
17 Regression analyzer
18 Network generator
19 Biomarker determinator

The invention claimed is:

1. A method for searching a biomarker to be used for determining whether or not a treatment has an effect on a disease, comprising:
   reading, from a storage, omics information of a plurality of patients before treatment and omics information of control;
   detecting signature molecular information peculiar to the disease from the omics information comprising a plurality of molecular information items, based on the read omics information of the plurality of patients and the read omics information of control; and
   obtaining a biomarker from the signature molecular information by repeating following steps (a) to (f):
   (a) selecting at least one molecular information item to be processed from the signature molecular information,
   (b) reading the clinical information of the plurality of patients before treatment and the information of the effect of treatment in the plurality of patients from a storage,
   (c) carrying out a regression analysis using the effect of treatment as an objective variable, and using the clinical information before treatment and variable data of the molecular information to be processed as explanatory variables,
   (d) generating a network structure based on partial correlation between a first node, a second node and a third node, the first node being the effect of treatment, the second node being the clinical information before treatment, and the third node being the molecular information to be processed, when the determination coefficient of the regression analysis is equal to or more than a first threshold value, and
   (e) determining that there is a causal relationship between the molecular information to be processed and the effect of treatment based on the network structure, in a case that the third node indicating a molecular information to be processed is directly or indirectly linked to the first node indicating the effect of treatment, and (f) determining the molecular information to be processed as a biomarker, when there is the causal relationship;

stratifying the plurality of patients for which the treatment effectively works and for which the treatment does not effectively work using the determined biomarker as a patient stratification marker, and treating a plurality of patients by administration of a medicine, ventricular assist system (VAS), surgery, laser, or a stent according to the determined biomarker.

2. The biomarker search method according to claim 1, further comprising:

reading clinical information of the plurality of patients before and after treatment from a storage; and obtaining the effect of treatment based on the clinical information before and after treatment.

3. The biomarker search method according to claim 1, wherein methylation level information of genes, expression information of mRNA, and expression information of proteins are used as the omics information.

4. The biomarker search method according to claim 1, further comprising selecting a biomarker having a strong causal relationship between the molecular information to be processed and the effect of treatment.

5. The biomarker search method according to claim 1, further comprising: adjusting the treatment based on the determined biomarker and repeating steps (a) to (f).

6. The biomarker search method according to claim 5, wherein adjusting the treatment includes adjusting the dosing of a medicine.

7. A device for searching a biomarker to be used for determining whether or not a treatment has an effect on a disease, the biomarker search device comprising:

a first storage storing clinical information of a plurality of patients before treatment;

a second storage storing omics information of the plurality of patients before treatment;

a third storage storing omics information of control;

a fourth storage storing information indicating the effect of treatment in the plurality of patients;

a signature molecular information detector that detects signature molecular information peculiar to the disease from the omics information comprising a plurality of molecular information items, based on the omics information of the plurality of patients and the omics information of control;

a regression analyzer that carries out a regression analysis using the effect of treatment as an objective variable, and using the clinical information before treatment and variable data of at least one molecular information item selected as molecular information to be processed from the signature molecular information as explanatory variables;

a network generator that generates a network structure based on partial correlation between a first node, a second node and a third node, the first node being the effect of treatment, the second node being the clinical information before treatment, and the third node being the selected molecular information to be processed as the nodes, when the determination coefficient of the regression analysis by the regression analyzer is equal to or more than a first threshold value; and a biomarker determinator that determines that there is a causal relationship between the molecular information to be processed and the effect of treatment based on the network structure, in a case that the third node indicating a molecular information to be processed is directly or indirectly linked to the first node indicating the effect of treatment, and determining the molecular information to be processed as a biomarker, when there is the causal relationship; and wherein the determined biomarker is used as a patient stratification marker to stratify the plurality of patients for which the treatment effectively works and for which the treatment does not effectively work; and wherein a plurality of patients are treated by administration of a medicine, ventricular assist system (VAS), surgery, laser, or a stent according to the determined biomarker.

8. The biomarker search device according to claim 7 further comprising:

a fifth storage storing clinical information of the plurality of patients after treatment, and a therapeutic effect calculator that obtains the effect of treatment based on the clinical information before and after treatment, wherein the biomarker search device stores information of the obtained effect of treatment.

9. The biomarker search device according to claim 7, wherein methylation level information of genes, expression information of mRNA, and expression information of proteins are used as the omics information.

10. A non-transitory computer-readable medium storing a program for searching a biomarker to be used for determining whether or not a treatment has an effect on a disease, the program making a computer execute:

reading, from a storage, omics information of a plurality of patients before treatment and omics information of control;

detecting signature molecular information peculiar to the disease from the omics information comprising a plurality of molecular information items, based on the read omics information of the plurality of patients and the read omics information of control; and obtaining a biomarker from the signature molecular information by repeating following steps (a) to (f):

(a) selecting at least one molecular information item to be processed from the signature molecular information, (b) reading the clinical information of the plurality of patients before treatment and the information of the effect of treatment in the plurality of patients from a storage, (c) carrying out a regression analysis using the effect of treatment as an objective variable, and using the clinical information before treatment and variable data of the molecular information to be processed as explanatory variables, (d) generating a network structure based on partial correlation between a first node, a second node and a third node, the first node being the effect of treatment, the second node being the clinical information before treatment, and the third node being the molecular information to be processed, when the determination coefficient of the regression analysis is equal to or more than a first threshold value, and (e) determining that there is a causal relationship between the molecular information to be processed and the effect of treatment based on the network structure, in a case that the third node indicating a molecular information to be processed is directly or indirectly linked to the first node indicating the effect of treatment, and (f) determining the molecular information to be processed as a biomarker, when there is the causal relationship; and stratifying the plurality of patients for which the treatment effectively works and for which the treatment does not effectively work using the determined biomarker as a patient stratification marker to; and wherein a plurality of patients are treated by administration of a medicine, ventricular assist system (VAS), surgery, laser, or a stent according to the determined biomarker.

11. The non-transitory computer-readable medium according to claim 10, wherein the program makes the computer further execute:

reading clinical information of the plurality of patients before and after treatment from a storage, and obtaining the effect of treatment based on the clinical information before and after treatment.

12. The non-transitory computer-readable medium according to claim 10, wherein methylation level information of genes, expression information of mRNA, and expression information of proteins are used as the omics information.

13. The non-transitory computer-readable medium according to claim 10, further comprising selecting a biomarker having a strong causal relationship between the molecular information to be processed and the effect of treatment.

* * * * *